United States Patent [19]

Stacey et al.

[11] Patent Number: 4,795,448
[45] Date of Patent: Jan. 3, 1989

[54] SUCTION COLLECTION SYSTEM

[75] Inventors: Gary R. Stacey, Randolph; Wesley H. Verkaart, Duxbury; Thomas D. Headley, Wellesley; Edward T. Powers, Medfield, all of Mass.

[73] Assignee: Haemonetics Corporation, Braintree, Mass.

[21] Appl. No.: 139,461

[22] Filed: Dec. 30, 1987

Related U.S. Application Data

[60] Division of Ser. No. 894,731, Aug. 8, 1986, Pat. No. 4,740,202, which is a continuation of Ser. No. 660,472, Oct. 12, 1984, abandoned.

[51] Int. Cl.[4] .............................................. A61M 1/00
[52] U.S. Cl. ................................... 604/319; 604/146
[58] Field of Search .............. 604/146, 147, 319, 320, 604/321, 118-121; 15/DIG. 8, 347, 353

[56] References Cited

U.S. PATENT DOCUMENTS

| 3,648,698 | 3/1972 | Doherty | 604/319 |
| 4,275,732 | 6/1981 | Gereg | 604/320 |
| 4,516,973 | 5/1985 | Telang | 604/319 |

FOREIGN PATENT DOCUMENTS

| 931037 | 7/1973 | Canada | 604/320 |
| 1810801 | 6/1970 | Fed. Rep. of Germany | 604/319 |

Primary Examiner—Edward M. Coven
Attorney, Agent, or Firm—Hamilton, Brook, Smith & Reynolds

[57] ABSTRACT

A suction collection system particularly suitable for drawing fluids from a patient area and storing the fluids for later use or disposal, which is operable in any orientation of the device, thereby providing a field operable system which may be transported in battlefield conditions. The portable suction system consists of a cylindrical evacuating chamber with a top sealing cap. A suction port on the sealing cap is connected to the fluid collection bag, which consists of a laminar flexible plastic bag having an air permeable, liquid impermeable patch or portion through which air may pass for purposes of providing a vacuum suction, yet the collected fluids will remain in the bag. The suction power is provided by a vacuum pump which is electronically regulated by periodically energizing and de-energizing the pump to conserve power supply energy.

6 Claims, 7 Drawing Sheets

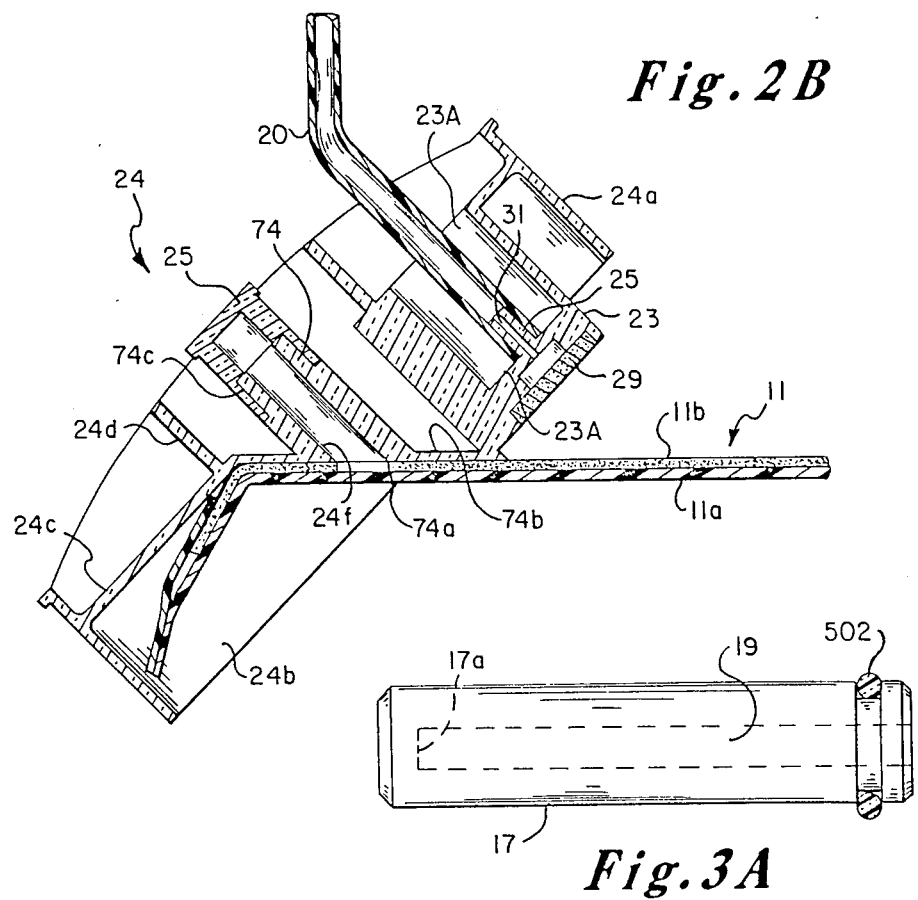
*Fig. 2B*
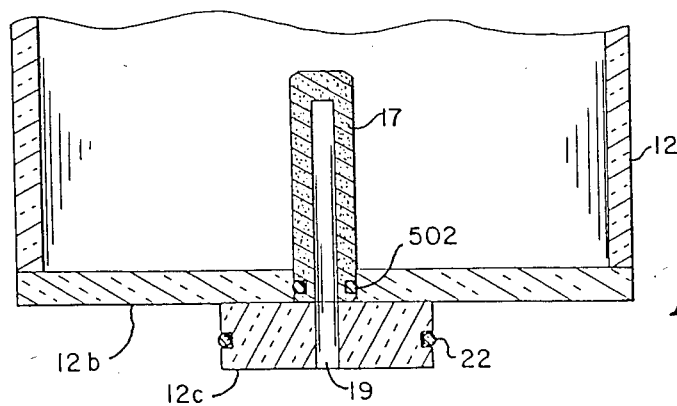
*Fig. 3A*
*Fig. 3B*

SHEET 2

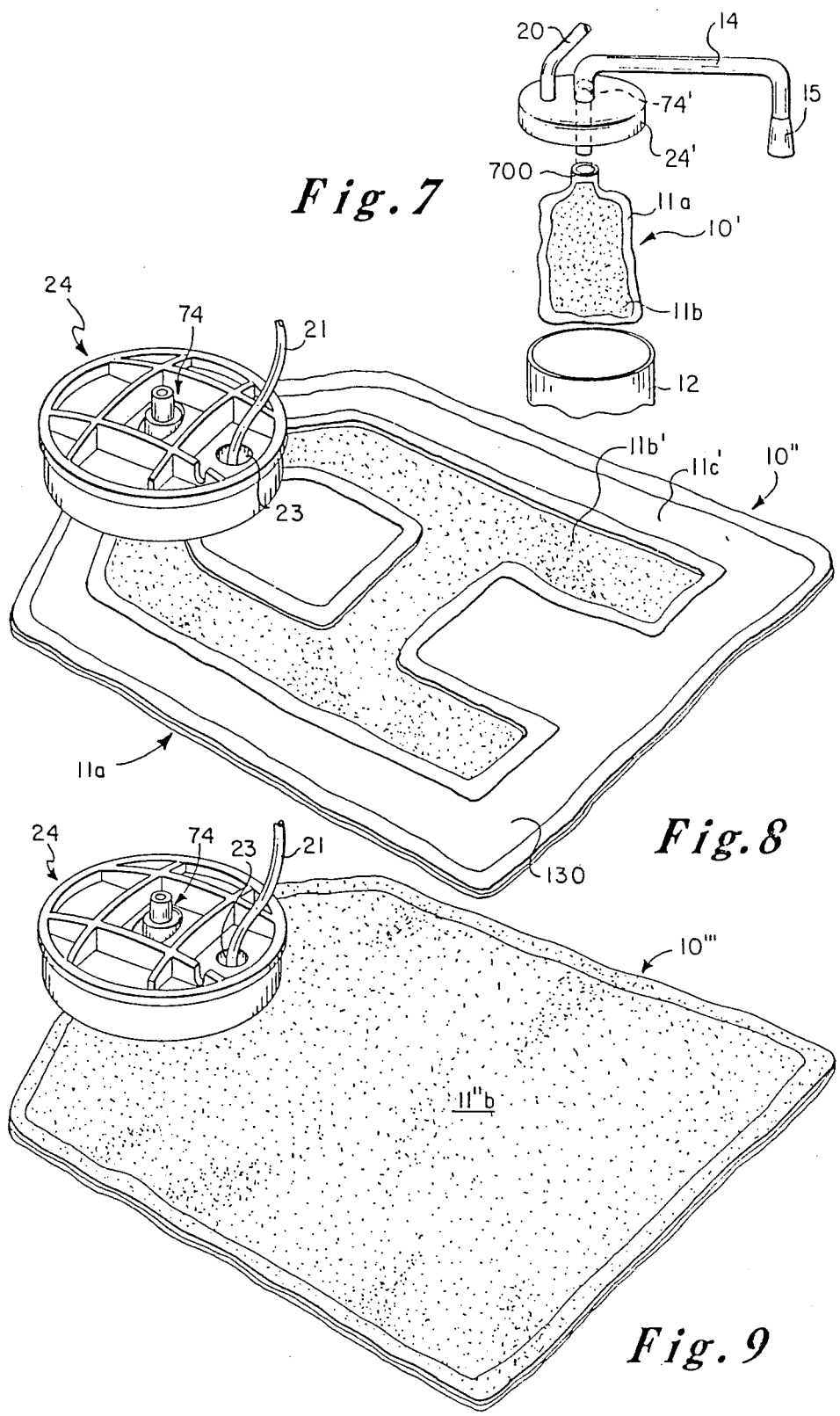

SUCTION COLLECTION SYSTEM

This application is a division of application Ser. No. 894,731 filed Aug. 8, 1986, now U.S. Pat. No. 4,740,202 which is a file wrapper continuation of Ser. No. 660,472 file Oct. 12, 1984, abandoned.

TECHNICAL FIELD

This invention is in the field of suction apparatus and, more particularly, relates to suction apparatus for drawing fluids from a patient area and storing the fluid in a disposable receptacle.

BACKGROUND ART

Suction devices are used in many medical applications to draw various fluids from the patient area and to store the fluids for later use or disposal. Suction devices have been utilized to draw aspirated fluids from a patient during a surgical operation and during the postoperative period. Suction devices are also used to drain fluids from the gastrointestinal tract, as well as to drain pulmonary mucous in tracheal incisions, and the like. Suction sources may be fixed or mobile. The fixed systems comprise wall vacuum outlets connected to a central system. The mobile systems are either relatively large capacity devices which are bulky or portable systems. Portable suction sources operate on power supplied by either electricity, compressed gas or manual power and may be used in a hospital, ambulance, home, or in the field. A summary of the state-of-the-art in portable suction devices is sent forth in *Health Devices*, March 1978, page 11 and pages 120–141.

In emergency conditions, such as in battlefield operations, it would be extremely desirable to have a portable suction device capable of continuous operation in any orientation. The known prior art suction collection systems are incapable of operation if the collection container tips over and falls in a sideways or upside-down position. Additionally, most prior art portable suction devices are calibrated for vacuum levels at one location and must be recalibrated if operated at different altitudes. Accordingly, a need exists for a relatively lightweight portable suction system capable of delivering regulated suction of precise vacuum and precise flow rate, which is capable of continuous operation in any orientation of the system.

DISCLOSURE OF THE INVENTION

The present invention relates to a compact, lightweight, portable suction system in which the vacuum for suction purposes is provided by evacuating a rigid plastic chamber or cannister having an end wall with an orifice connected to a vacuum pump and an open top sealed by a sealing cap. A disposable bag having a patch of semi-porous material is affixed to a suction port on the cap. The patch is made of hydrophobic material which has a porosity such that it is permeable to air and impermeable to fluids such as blood, as well as most bacterial matter. The suction port in the sealing cap, or cover, is fluidly connected to a suction tip. The collection bag is integrally attached to the sealing cap and this unit may be sterilized and handled as a disposable unit. Because the hydrophobic patch pores are impermeable to bacteria, the disposable unit, once internally sterilized, remains aseptically isolated from the outside environment.

In operation, the rigid chamber, or cannister, is evacuated by the vacuum pump, thus drawing air and fluids through the suction port into the suction tip into the flexible collection bag with the hydrophobic patch where the liquids are retained for collection. The air passes through the semiporous material and through the orifice on the end wall of the chamber and into the vacuum pump where it is exhausted. A check valve is provided between the vacuum pump and the chamber to prevent backflow of air and to vent the vacuum pump to atmosphere through a solenoid valve when the pump is off. In this manner, the negative pressure in the vacuum pump is relieved so that when the pump starts again, it does so under no load conditions.

An electronic regulator maintains the required vacuum by cycling or periodically energizing and de-energizing the vacuum pump. In a preferred embodiment, the device is battery powered. The use of electronic regulation of vacuum by cycling the pump instead of conventional mechanical regulation, conserves battery power and extends the useful operating time between charges.

Additionally, the battery may be recharged by means of an external charger or via a photovoltaic array provided with the system. Nine preset vacuum levels are provided by a simple switch mechanism. In addition the vacuum may be continuously varied over a wide range. The vacuum level is displayed on a control panel meter. Continuous or intermittent vacuum may be selected from the control panel. The device will operate in any orientation.

Intermittent suction flow may be preselected for a period of time "On" and a different period of time "Off". The intermittent On and Off periods may be varied by internal adjustments.

BRIEF DESCRIPTION OF THE DRAWINGS

FIG. 1A is a section along lines 1A—1A of FIG. 1.

FIG. 2B is a sectional view along lines 2B—2B of FIG. 2.

FIG. 3A is a side view of the fluid stop tube 17.

FIG. 3B is a sectional view of the bottom portion of container 12 with stop tube 17 in place.

FIG. 7 is a schematic view of an alternate embodiment of the invention.

FIG. 8 is a perspective view of a further embodiment of the disposable unit of the invention.

FIG. 9 is a perspective view of another embodiment of the disposable unit of the invention.

BEST MODE OF CARRYING OUT THE INVENTION GENERAL DESCRIPTION

Figure 1:
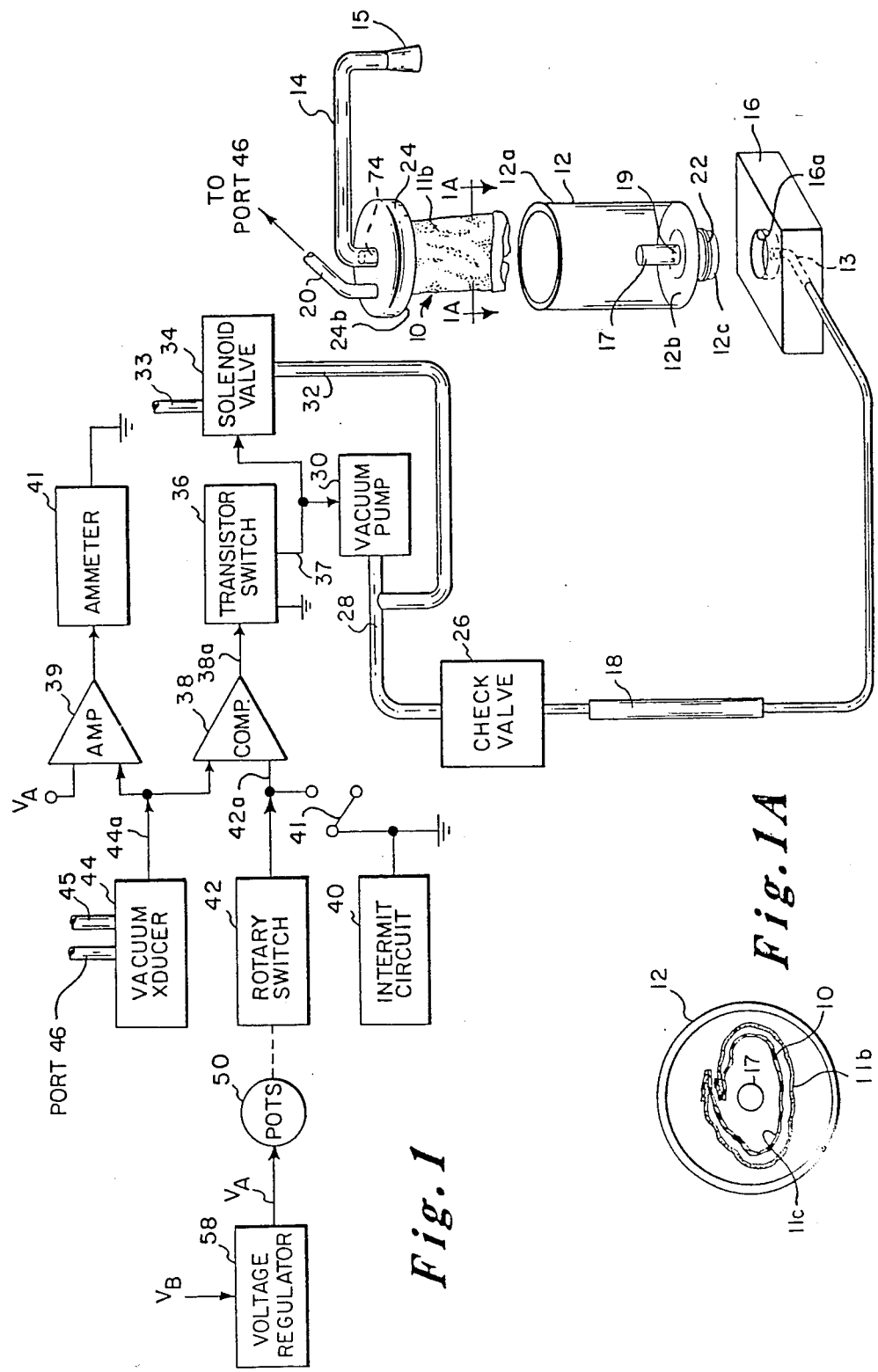
FIG. 1 is a block diagram of a preferred embodiment of the invention showing the general electromechanical features thereof.

Referring now to the block diagram of FIG. 1, an overall general description of the suction system will be provided in connection therewith prior to a detailed description of specific items. As may be seen in FIG. 1, a suction tip 15 is connected by a fluid conduit 14 to a suction port 74 on a plastic sealing top cover 24. Conduit 14 is affixed to a nipple on the external side of suction port 74, such as by well-known heat sealing means; or a press fit connection may be made.

The interior side of port 74 extending through the bottom of cap 24 is coupled to an input port or opening on one side of flexible container bag 10. Bag 10 is partially formed of hydrophobic material 11b which is impervious to fluids such as blood yet permits air to pass through its pores. Bag 10 is affixed to port 74 in such a manner as to be readily folded about itself, as shown in FIG. 1A, so as to fit inside circular container 12. This enables a large volume of liquid to be accumulated in the bag which expands to almost fill the relatively small cylindrical container. A continuous airway is formed by the vacuum sensor tube 20 and a second small cap inlet 25 (See FIG. 2B) which extends through cover 24 into chamber 12.

The cap 24, collector bag 10, port 74 and tube 20 form an integral disposable unit which may be capped and sterilized and provided in an aseptic package for disposable usage. The inner periphery 24b of cap 24 is adapted to form a vacuum tight fit with the outer cylindrical wall 12a of chamber 12.

Chamber 12 is a rigid plastic light transparent cannister of cylindrical shape having an exterior wall surface 12a and a bottom wall 12b with a projecting portion 12c to which is affixed on O-ring seal 22. the cylindrical shape is preferred since it is desired to seal the top and a circular cover 24 over the circular opening forms a self-sealing structure unlike other possible shapes. Chamber 12 is adapted to be removably mounted on block 16 by inserting the projecting portion 12c into a corresponding opening 16a in block 16 whereby the O-ring 22 forms a vacuum seal against opening 16a.

An orifice 19 is provided through projecting portion 12c. Orifice 19 mates with conduit 13 extending through block 16. A fluid stop tube 17 mates with orifice 19 to prevent flow of fluid into the system in the event bag 10 should rupture.

Thus, when chamber 12 is mated with block 16 and bag 10 inserted in chamber 12 and sealing cap 24 covers the chamber, a complete air suction/vacuum path is provided from tip 15 to conduit 13 in block 16.

Conduit 13 is coupled through access viewing tube 18 to check valve 26 which in turn is coupled to the output port of vacuum pump 30 and solenoid valve 34. Solenoid valve 34, which is operated by transistor switch 36, vents vacuum pump 30 to atmosphere via port 33 during time intervals when the pump is off for the purpose of removing negative pressure to allow the pump to re-start under no load conditions.

Suction is generated by vacuum pump 30 which is energized and de-energized by transistor 36. The vacuum may thus be electrically controlled by operation of transistor 36, as will be described below.

The vacuum in chamber 12 is sensed by vacuum transducer 44 via port 46 which is coupled to tube 20 on cap 24. Vacuum transducer 44 converts actual vacuum from chamber 12 to an analog voltage signal which is coupled via lead 44a to one input terminal of voltage comparator 38. The other input terminal of voltage comparator 38 is normally coupled to a vacuum control voltag signal from rotary switch 42 via lead 42a.

If the control voltage signal differs from the vacuum voltage signal at the input leads to the comparator 38 an output signal appears on lead 38a which biases transistor switch 36 ON causing a current path to be completed to ground through the solenoid of valve 34 and the motor windings of vacuum pump 30 via lead 37 until such time as the voltages at the input to comparator 38 are equalized in which case the vacuum in the chamber is at the level commanded by the setting of switch 42.

The control voltage signal is set by the operator's selection of one of many positions of switch 42 which is tied to the center taps of a plurality of multi-ganged potentiometers 50 fed a reference voltage $V_A$ by voltage regulator 58. In one position of switch 42, a continuously variable potentiometer may be selected whereby the operator may continuously vary the vacuum setting.

Voltage regulator 58 regulates the voltage $V_B$ from the battery or other power supply used by the unit to provide a regulated reference voltage $V_A$ of 5.0 volts D.C. which is coupled to potentiometers 50 and additionally through a resistor to an input lead of amplifier 39 wherein the reference voltage may be summed with the vacuum voltage signal from transducer 44 and the summed signal displayed on ammeter 41 as a measure of the actual vacuum in chamber 12.

An intermittent circuit 40 comprising a transistor switch controlled by a multivibrator oscillator may be connected to the output lead 42a of switch 42 to periodically ground one of the inputs to comparator 38 thereby periodically interrupting the operation of pump 30.

Disposable Unit

Figure 2:
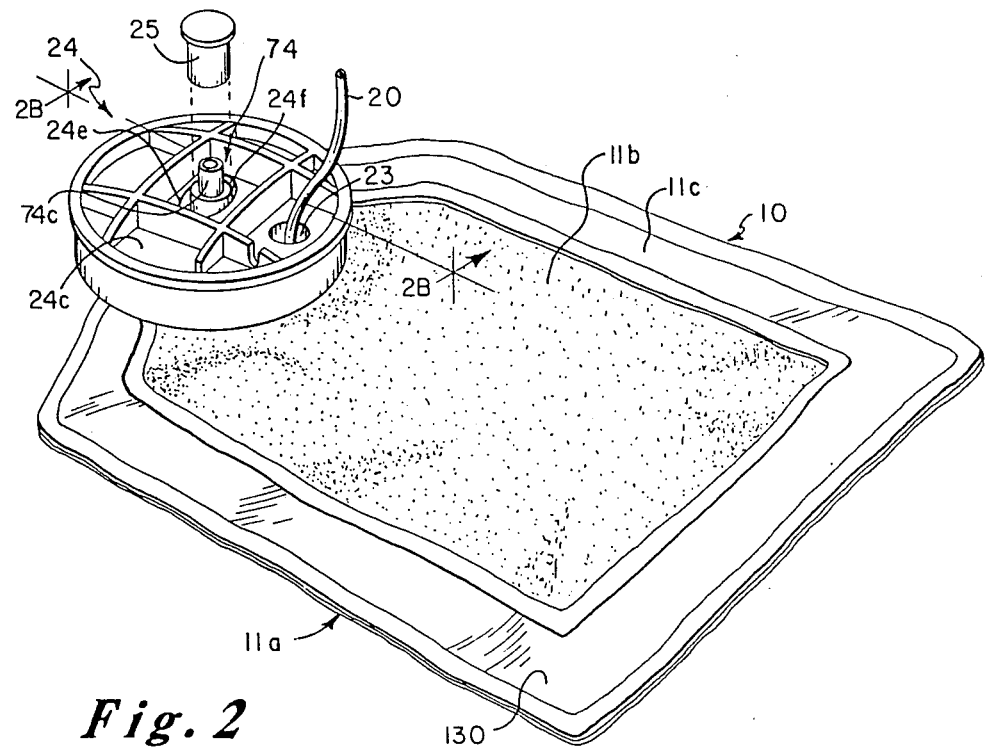
FIG. 2 is a top perspective view of the suction bag and integral sealing cap disposable unit of the suction system of the invention.
Figure 2A:
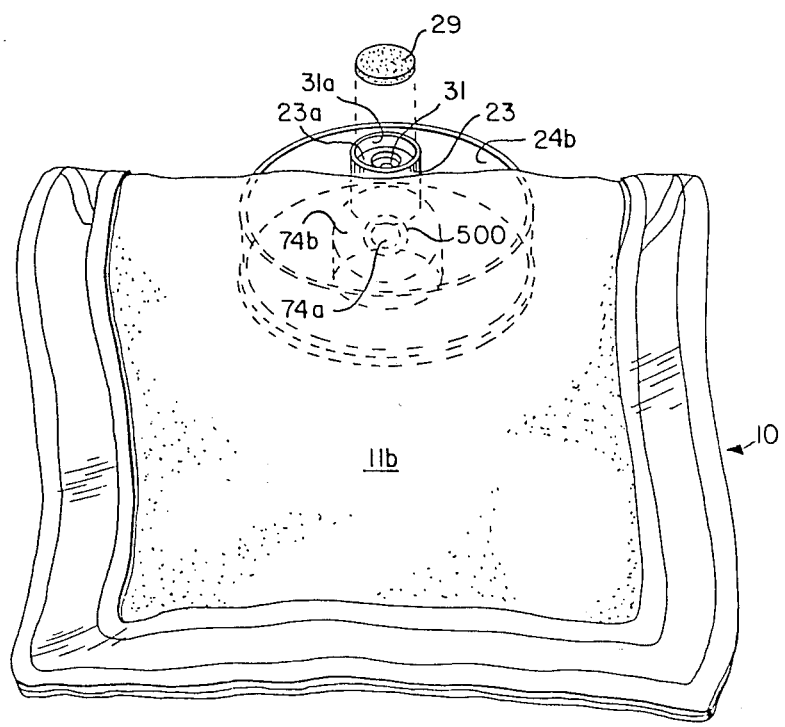
FIG. 2A is a partially exploded bottom perspective of the unit of FIG. 2 with the suction bag folded back on itself.

Referring now to FIGS. 2, 2A and 2B, the details of the disposable bag/cap unit will be explained. FIG. 2 is a top perspective view with the bag 10 lying flat and the top external surfaces of sealing cap 24 shown in detail. FIG. 2A is a bottom perspective view of the bag/cap unit with bag 10 folded back on itself to show the details of the pressure sensor port 23. FIG. 2B is a section through lines 2B—2B of FIG. 2.

Bag 10 consists of a first planar sheet 11a of polyethelene plastic. The plastic sheet 22a on the side away from the viewer in FIG. 2. A second planar sheet 11b of semi-porous material is provided on the opposite side. Sheet 11b is a laminate of porous polytetrafluoroethylene and polyester fabric having a suitable pore size to enable passage of air but prevent passage of liquid and/or most bacteria. Sheet 11b is heat sealed along its borders to a third sheet 11c of non-porous polyethelene centrally cut out to conform to the outer border of semi-porous sheet 11b. Sheet 11c is in turn heat sealed to the outer border of bottom sheet 11a; and forms an air and liquid impervious sealed frame around semi-porous patch 11b. Air can pass through sheet 11b but not through the remaining bag surfaces and because of the porosity of sheet 11b, liquids such as blood will not pass through any of the bag surfaces. The pore size for sheet 11b depends upon the surface tension which the material generates on the liquid and the desired breakthrough pressure. A pore size of 0.1 micron to 0.2 microns is suitable for a polytetrafluoroethylene/polyester laminate at breakthrough pressures of 20 psi to 7 psi.

It is important to note that while bag 10 may be entirely fabricated of hydrophobic material 11b, as shown in FIG. 9, the embodiment shown herein in FIGS. 2 and 2A is preferred for cost reasons since such material is much more expensive than the non-porous material 11a or 11c. It will be realized that since the bag and cap unit is intended to be provided as a disposable unit, which is used once and then discarded, cost is an important factor.

However, as will be explained in detail in connection with FIG. 8, when fabricating the bag 10 with porous and non-porous portions, it is vital that the porous portions be of adequate length and breadth and located such that when disposed in the container 23, the porous portion is positioned so that in any orientation of the container, a surface of the porous material will not be covered by collected liquid until the desired liquid level is reached. Otherwise, suction will be lost in when the porous portion is completely covered by liquid.

Thus, in the preferred embodiment shown herein, the bag 10 is configured with respect to the inner diameter of container 12 so that in order to insert the bag into the container, the bag must be folded into a generally cylindrical shape with the porous patch on the exterior, as shown in FIGS. 1 and 1A. Also, the patch extends in height and width along substantially the entire surface of one side of bag 10.

An inlet opening 500 is provided in sheet 11 on the porous patch 11b. The bag 10 is affixed to inlet port 74 by centering opening 500 on the port opening 74a and gluing or heat sealing a portion of sheet 11 about the periphery of the opening 500 to a planar flange portion 74b of port 74. This method of affixing bag 10 to cap 24 enables one to form a low-cost planar bag using current machinery. The precise location of opening 500, either on the porous patch or non-porous surfaces, is not critical since the bag is operable in any position. Port 74 extends through an oval opening 24e in a planar top surface 24c of cap 24 from which external reinforcing ribs 24d extend externally in a plane normal to surface 24c. An inner sealing surface 24b of cap 24 extends downwardly from the top surface 24c about the circular periphery of cap 24.

A nipple portion 74c of port 74 extends outwardly from cap surface 24c through the oval opening in 24e in cap surface 24c. A cylindrical wall 24f extends from opening 24e to bottom surface 74b of port 74. Bottom surface 74b intersects the plane of cylindrical wall 24f at an angle forming a circular opening 74a at the base of port 24.

An optional cover 25 for the nipple portion 74c of port 74 is provided with the disposable unit. Cover 25 forms a press fit over the nipple portion of port 24 and, of course, is removed prior to operation of the unit.

As shown in FIG. 2B pressure sensor tube 20 extends into a circular opening 23a formed at one end of cylindrical tube 23 integral with cup 24. Tube 20 is affixed at the bottom to a nipple 2 having an opening 31 at the bottom wall 23a of tube 23. A disk 29 of porous plastic material is affixed by adhesive or heat bonding to the bottom of tube 23 covering opening 31.

Disk 29 is preferably formed of porous polyethelene, a material having pores of sufficient porosity to be permeable to air but which clog when contacted by fluids. A suitable pore size is in the order of 20 microns. The function of disk 29 is therefore to prevent backflow of fluid from bag 10 into vacuum transducer 44 (FIG. 1) which is connected to chamber 12 via tube 20. Such backflow may occur if bag 10 should break with fluid in it during pump operation.

Chamber

Figure 3:
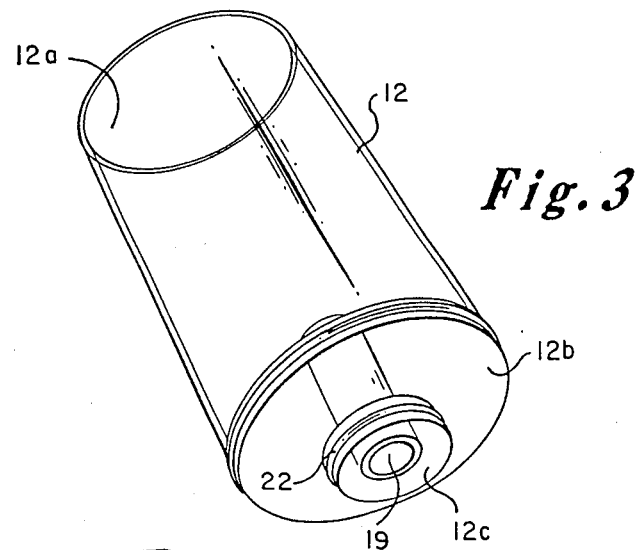
FIG. 3 is a side perspective view of the rigid container of the inventoon.

The details of chamber 12 are shown more clearly in FIGS. 3, 3A, and 3B. Chamber 12 is formed of rigid plastic material such as polycarbonate and has an outer cylindrical wall 12a, an end wall 12b, and an open top adapted to be sealed by cap 24 (previously mentioned in connection with FIG. 2).

A tubular orifice 19 extends through a projecting portion 12c of end wall 12b. Orifice 19 extends along the length of fluid stop tube 17 until terminated at top wall 17a of tube 17.

Tube 17 is formed of the same porous polyethelene material as disk 29 and performs a similar function. In the event bag 10 ruptures for any reason while within chamber 12, any fluids within bag 10 will be prevented from passing through orifice 19 since the fluids will clog up the pores of tube 17.

Fluid stop tube 17 is removably mounted to bottom wall 12b of chamber 12 by an O-ring seal 502 within an annular groove 21 on tube 17. Projection 12c with corresponding O-ring 22 is used to removably affix chamber 12 to wall 16a (FIG. 4) of base block 16.

Packaging

Figure 4:
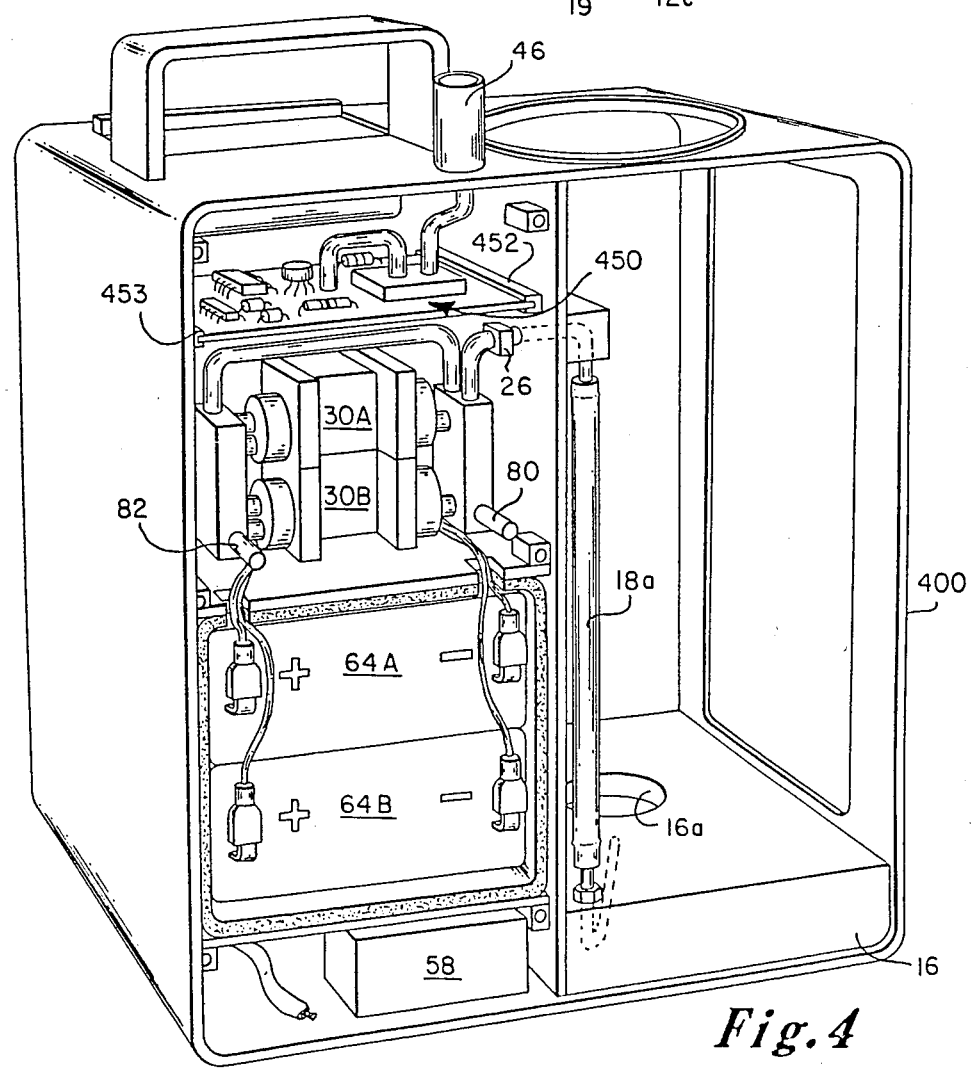
FIG. 4 is a side perspective view of the suction system housing showing the vacuum pumps and other portions of the invention.

Referring now to FIG. 4, the packaging of the suction system of the invention may be shown in detail. The electronic control circuitry is provided on a panel 450 which may slide into carrying case 400 on rails 452 and 453. The vacuum pumps 30A and 30B are located below the control panel. Exhaust ports 80 and 82 are provided to decrease the noise of the pumps. Batteries 64A and 64B are stored below the pump and the D.C. charger supply 58 is located below the batteries.

Figure 5:
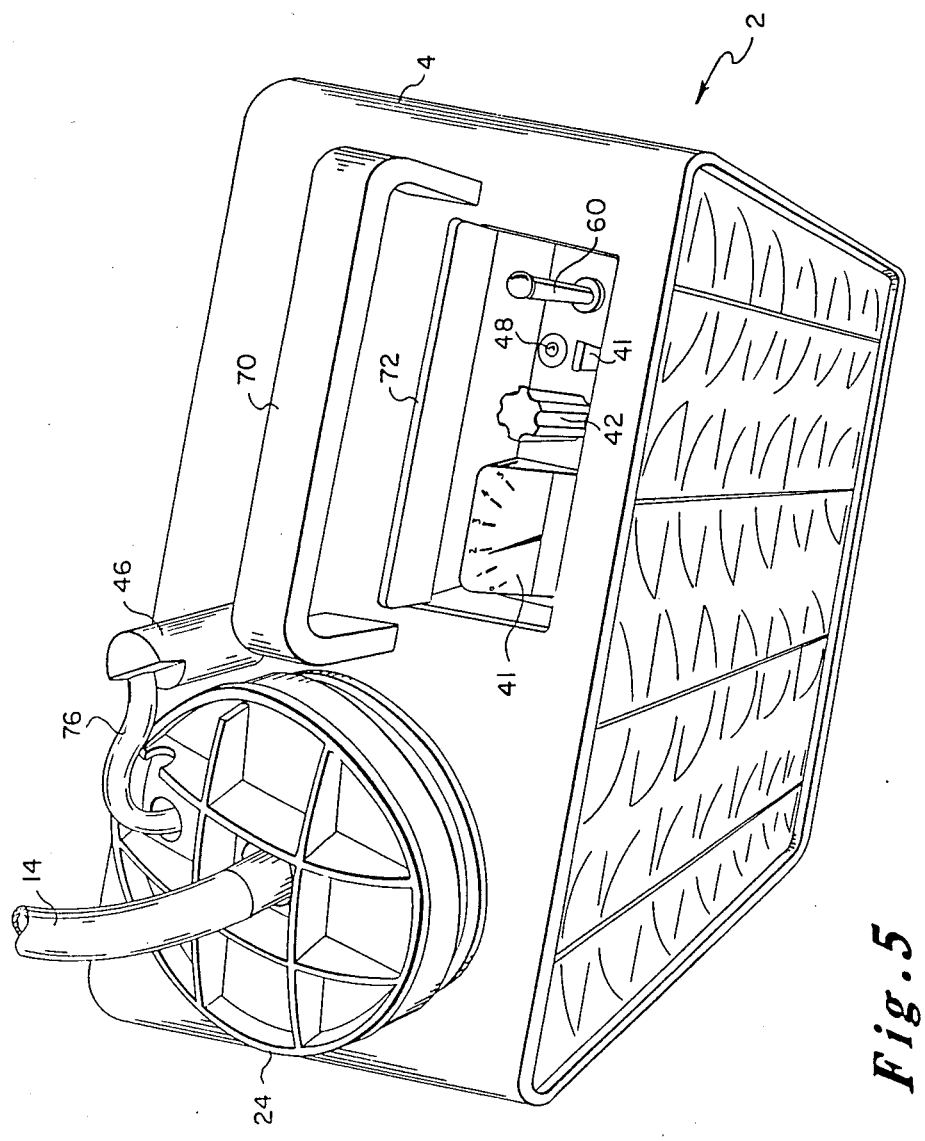
FIG. 5 is a top perspective view of the suction system showing the control panel.

The instrument panel is shown in FIG. 5 to comprise an ammeter 41 for displaying vacuum levels, a rotary switch 42 for selecting vacuum levels, battery level LED 48, power switch 41 and spring illuminating switch 60. The panel is recessed within a protective covering plate 72. Handle 70 is provided at the top of the carrying case.

Electromechanical System

Figure 6:
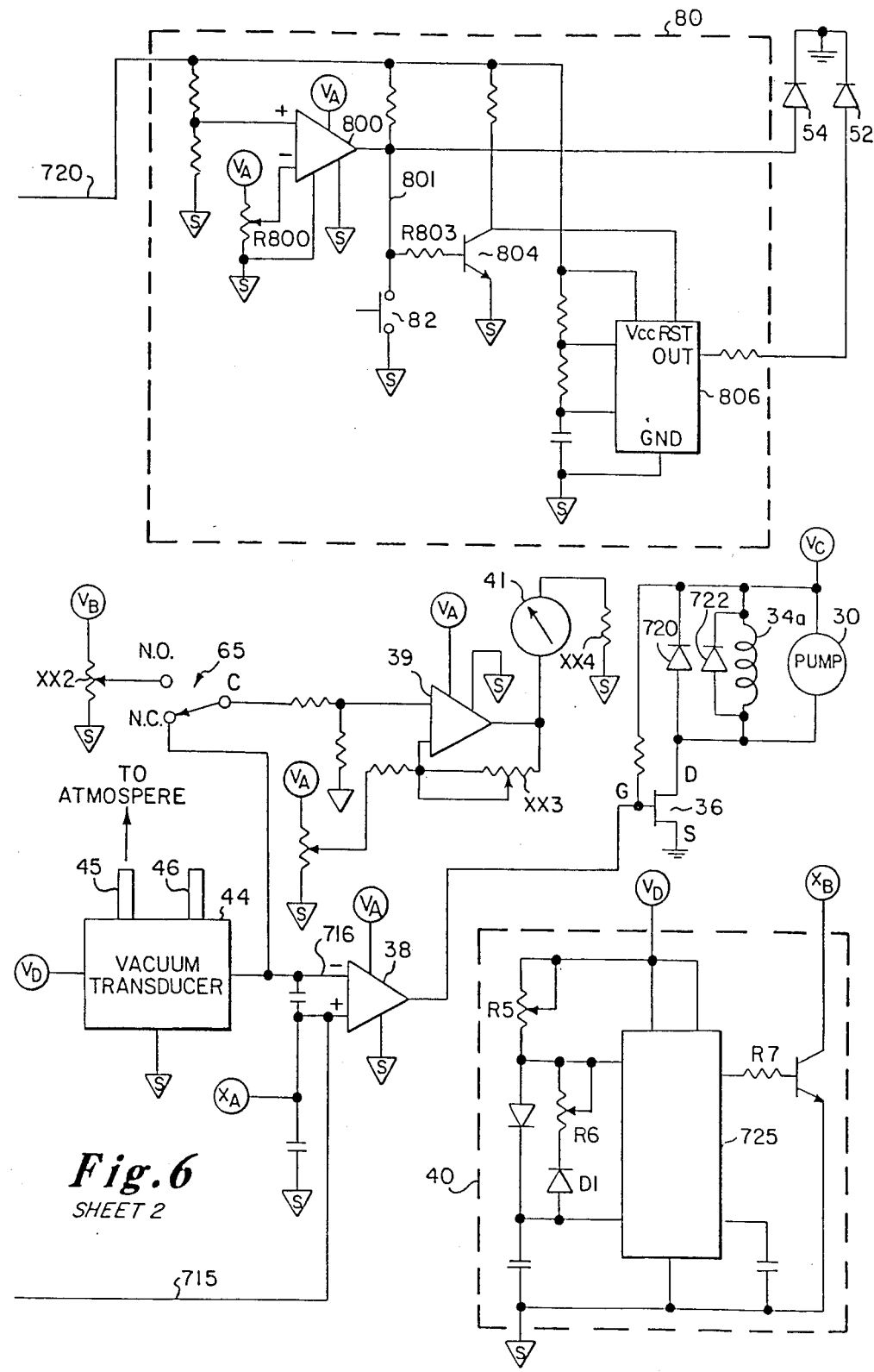
FIG. 6 is a detailed schematic drawing on two sheets of the electro-mechanical portions of tee preferred embodiment of FIG. 1.

The details of the electromechanical portions of the invention will be explained in connection with the schematic of FIG. 6. Like numeral references with other figures are utilized in FIG. 6.

Starting with the voltage supply 64 it may be seen that two 6-volt batteries 601 and 602 are connected in series from ground, or the negative side, through 3 amp circuit breaker 604 to spring return switch 60. When switch 60 is in the normally on (N.O.) position about 14 volts is applied to two illuminating lamps 48A and 48B on the control panel. Battery 601 is coupled in series through circuit breaker 603 to arm 605A of power switch 605. In the ON position, switch arm 605A provides 14 volts to D.C. regulator 58a. A solar cell 606 is connected in parallel with the two batteries between ground and the anode side of diode 607. Diode 607 provides unidirectional current from solar cell 606 to continuously charge batteries 601 and 602 and to prevent reverse current flow to the solar cell.

A battery charging circuit may be supplied from a conventional A.C. transformer adapter (not shown) coupled across input jacks 701 and 703. Alternatively, if a battery supply having a voltage between 14 and 40 volts D.C. is available, it may be coupled across jacks 702 and 703 to supply internal battery charging current. This voltage is regulated down to the correct voltage for charging the two batteries by voltage regulator 900. Diodes 704, 705 and 706 protect the regulator 900 from reverse current flow. Adjustable potentiometer 709, in series connection with resistor 708, is used to adjust the charging voltage to the correct level. Capacitor 710 is a filter used to reduce noise ripple effects.

The voltage from voltage supply 64 is coupled through arm 605A of power switch 605 to D.C. regulator 58a. D.C. regulator 58 is a commercially available regulator made by National Semiconductor Company, Model LM2931. Regulator 900 (previously mentioned) is a Model LM317K, available from the same source.

The regulated output voltage from D.C. regulator 58 is labelled $V_A$ and is supplied throughout the schematic at various terminals, also labelled $V_A$. The unregulated D.C. voltage $V_D$, provided at the input to regulator 58 is coupled via lead 720 to voltage test circuit 80 (sheet 2) and a number of other places throughout the schematic, which are also labelled $V_D$.

Regulated voltage $V_A$ is coupled to one side of 9 potentiometers, labelled VR1, VR9, in potentiometer assembly 50. The center tap of each potentiometer is coupled to separate terminals a-i on rotary switch 42. The potentiometer resistors are coupled together in parallel and grounded on one side, thus various voltages, depending on the position of the center tap of each potentiometer may be coupled to the terminals 42a-i of 10 position rotary non-shorting switch 42.

An additional 100,000 ohm single turn potentiometer VR10 is coupled in parallel with the other potentiometer to terminal j of rotary selector switch 42. One side of this potentiometer, VR10, is coupled through 1,000 ohm resistor R3 to the regulated voltage supply 58 and the other side of VR10 is coupled to ground. Thus, any one of the nine pre-set voltages from potentiometers VR1-VR9, may be coupled through selector switch 42 to the input side of comparator 38 for setting the vacuum level in the chamber 12. Alternatively, the vacuum level may be continuously varied by potentiometer VR10 in the "j" position of selector switch 42. As will be explained, the vacuum level may be varied, in this fashion, from 0 to 250 centimeters of water. The output of rotary selector switch 42 is coupled through lead 715, as previously mentioned, to the + input of voltage comparator 38 (See sheet 2), where it provides a control voltage for setting the vacuum.

The minus terminal of voltage comparator 38 is coupled via lead 716 to the output lead of vacuum transducer 44. Vacuum transducer 44 may be a commercially available device, such as a 142PC05DL manufactured by Microswitch Company, a division of Honeywell Company. Vacuum transducer 44, as previously mentioned, is coupled via port 46 to vacuum sensor port 20 so as to sense the differential vacuum (or negative pressure) within chamber 12 with respect to atmospheric pressure sensed by port 45. The vacuum transducer 44 generates an electrical voltage signal proportional to the instantaneous value of the differential vacuum. This signal is compared in voltage comparator 38 with the control voltage via lead 715 from selector switch 42.

An output electrical signal is provided from comparator 38 as an input to the gate terminal, G, of a field effect (FET) transistor switch 36. The source terminals of FET switch 36 is coupled to ground and the drain terminal D of switch 36 is coupled to the anodes of suppressor diodes 720 and also to one side of the solenoid coil 34a and one side of the windings of the motor of pumps 30. Pumps 30 are dual vacuum pumps powered by a brushless D.C. motor (not shown).

Thus, in normal operation, a voltage difference between the two input signals to comparator 38 means that the negative pressure in chamber 12 differs from the desired setting of potentiometers 50. A voltage output signal is generated by comparator 38 in response to this voltage difference and this voltage output signal biases FET 36 ON to complete a current path from the 6 volt battery supply at 605B labelled $V_c$ to ground through the solenoid 34a of the solenoid valve 34 and the motor windings (not shown) of vacuum pump(s) 30. The pump(s) 30 are thereby energized. At the same time, current through the solenoid closes valve 34 (FIG. 1) blocking the fluid vent path 32 to port 33 and atmospheric pressure.

Pump 30 continues to run until the negative pressure in container 12 attains the level indicated by the potentiometer 50 settings, at which time, the voltage difference between the two input signals to compacator 38 is nulled and no output biasing voltage will be coupled to the gate terminal of FET 36 causing the FET to stop conducting. This opens the circuit path to ground from $V_c$ through the pump 30 motor windings, thereby automatically stopping the pump motor(s) 30 when the correct vacuum level is reached The circuit path from $V_c$ through the solenoid coil 34a is also opened and the solenoid valve is de-energized to vent the pump 30 to atmosphere to remove the load on the pump when it is started again.

In the intermittent mode of operation which further conserves battery current, switch 41 is placed in the intermittent position, thus connecting the terminals labelled XB (sheet 2) and XA (sheet 1) together. This connection provides a coupling path for the intermittent circuit 40 to short-circuit the control voltage, on lead 715, to ground at intervals of time determined by the intermittent circuit 40. Intermittent circuit 40, as may be seen, consists of a multivibrator 725 in which the Off-time and On-time of the multivibrator are independently controlled by the setting of the Off-time potentiometer R5 and the On-time potentiometer R6.

Multivibrator 725 may comprise a commercially available multivibrator, such as an NE555. Resistor R6 is a 1 megohm resistor which is coupled through diode D1 to an input lead of multivibrator 725.

A battery test circuit 80 is provided wherein one-half of the unregulated battery voltage Vd on line 720 is coupled to the + side of voltage comparator 800. The other − side of voltage comparator 800 is provided with regulated voltage from D.C. regulator 58 at the terminal marked $V_A$ through multiturn trimpot potentiometer R800. The setting of potentiometer R800 establishes the low point of suitable operating battery voltage.

When the battery voltage is above the low battery voltage setting, the output of the comparator 800 is high and the green LED 54 is illuminated. When the output of comparator 800 is high, transistor 804 is biased to conduct, which holds multivibrator 806 in the reset mode. Multivibrator 806 is an oscillator. When it is held in a reset mode, its output is held low. Therefore, the red LED 52 coupled to its output is "Off". When the battery voltage drops below the low point determined by the setting of potentiometer R800, it is sensed by comparator 800 and the comparator goes "low". The green LED 54 goes "Off". Transistor 804 stops conducting. The reset voltage level to multivibrator 806 goes high and the multivibrator is no longer in the reset mode. The multivibrator now oscillates and turns the red LED "On" and "Off". Note: The green and re LEDS 52 and 54 are combined into one single package and to the user appear to be a single light. Vacuum level is displayed on meter 41. The vacuum signal from transducer 44 is summe with zero adjust pot 21 with amplifier 39. Potentiometer 23 provides "full scale" gain adjustment. Alternately, battery voltage is displayed on meter 41 when spring return switch 65 is activated. Potentiometer 22 scales battery voltage VB to amplifier 39's gain setting. Meter 41 is a 0–100 μa meter and resistor 24 converts the output voltage of amplifier 39 into the correct current for the proper meter operation.

It is important to note that the vacuum transducer 44 is a differential device. It has one port 45 that is coupled to atmospheric pressure and a second port 46 which is coupled to the interior of vacuum chamber 12. So, the device 44 is continuously comparing the vacuum chamber negative pressure against atmospheric pressure and providing a voltage signal proportional to the difference between the two. Thus, the calibration of the device is not affected by changes in atmospheric pressure which might come about from either changes in the weather or, more importantly, changes in altitude during use.

Portability, and hence weight, of the apparatus is an important consideration for the environment in which the suction collection system may be utilized. It is therefore desirable to minimize the weight of the batteries and to maximize the running time of the pumps. In a conventional vacuum pump suction system, the pump runs continuously. A mechanical regulator limits the amount of maximum negative pressure developed at the suction tip. The mechanical regulator is a diaphragm device biased by a spring which opens a passageway that allows outside air to enter into the pump. The pump is constantly running at full capacity while the mechanical regulator limits the maximum amount of negative pressure that is available at the suction tip.

In the present device, the actual vacuum in the chamber is sensed and the pump turned "on" and "off" electronically. The dead volume of the pump is very small, relative to the volume of the collection chamber and the tubing so the duty cycle of the pump can be regulated to maintain very precise levels of vacuum. Turning the pump "on" and "off" has the battery conservation advantage of not requiring power when the pump is "off". In low suction flow conditions, such as chest drainage applications, where a maximum of about 50 to 100 mls per minute flow is required, the amount of suction required is very small. So, to maintain a negative pressure of 30 or 40 centimeters, the pump needs to be "on" only a very small percentage of the time.

Another important advantage of the system above described, is the ability to dial in any desired maximum negative pressure and have the pump operate to that instantly when the system is turned "on". With a mechanical regulator, there is no absolute calibration. Instead, the suction tubing is . occluded and a mechanical gauge is read and adjustments made to the regulator until the desired pressure is reached. In the present device, it is only necessary to set one potentiometer to the desired vacuum level, which is displayed on meter 41, turn on the device and that is the instantaneous maximum negative pressure.

An alternate embodiment of the suction collection system will now be described in connection with FIG. 7, wherein parts similar to those shown in FIG. 1 will contain a like numeral designation and modified parts will carry a like designation with a prime suffix. The container 12 of FIG. 7, while not shown in detail, is in all respects substantially the same as the container, as shown in previous figures. Bag 10' is a fluid collection bag having a air permeable, liquid impermeable portion 11b and an impermeable sheet 11a similar to the construction shown in FIG. 1. However, in the embodiment of FIG. 7, bag 10' is not formed integral with the cover cap 24'. Instead, a plastic nipple 700 is affixed to an opening at the top of bag 10', such as by heat-sealing or other suitable adhesion techniques.

Nipple 700 may then be suitably attached to fluid coupling port 74' which is, in turn, affixed to the top of cap 24'. Conduit 14 is also affixed to the external end of port 74' and a suction tip 15 attached to the remaining end of fluid coupling conduit 14. In all other respects, the cap 24' may be similar to cap 24 shown in FIG. 1, including the vacuum sensing port tubing 20, which is coupled to the vacuum transducer.

The bag embodiment of FIG. 7 has the advantage of lower cost manufacture. However, there are certain disadvantages connected with the problem of providing an aseptic port 74' if the cap is intended to be reused, as would be the intent in going to the embodiment shown in FIG. 7. There are also disadvantages associated with the ability to provide an adequate seal between the bag 10' and the nipple portion 700. These disadvantages make the embodiment shown in FIG. 1 and previously described, more preferable at the present time.

FIGS. 8 and 9 show alternative embodiments of the invention in which the dimensions of the porous portion 11b are varied. In all other respects, the bags are similar to that shown in FIG. 2, described previously. The bag 10'' in FIG. 8 is affixed to the cap 24 in the manner previously described and is intended to form an integral disposable unit which may be sterilized and disposed of after use. The embodiment of FIG. 8 differs from that of FIG. 2 in that the porous portion 11b' is formed in a generally H-shaped configuration thereby utilizing less porous material and therefore resulting in a lower cost disposable bag. The H-shaped embodiment still retains sufficient length and breadth when folded about itself and disposed in a cylindrical container, such that a portion of the porous material will always be exposed above fluid collected in the bag in any orientation of the chamber up to the desired vertical height of collection desired.

In the embodiment of FIG. 9, the entire embodiment of 10''' is made of porous material 11''b and is otherwise identical to and intended to be secured to cap 24 in the manner shown n connection with FIGS. 2 and 2A. This embodiment has the advantage of simplicity and ease in manufacture and may be preferred in those applications where the cost of the porous material is not significant with respect to the intended usage.

Equivalents

This completes the description of a preferred embodiment of the invention. Those skilled in the art may recognize other equivalents to the specific embodiment described herein, which equivalents are intended to be encompassed by the claims attached hereto.

We claim the following:

1. A flexible bag for collecting fluids which is adapted to be disposed in a vacuum chamber; said bag being formed of two sheets of flexible plastic material sealed at the peripheral edges forming two planar surfaces, at least one such surface having a porous portion forming an air permeable/fluid impermeable path to the interior of said bag, such that when introduced into said chamber, an air suction path for collecting fluids is established, the portion having sufficient surface area in two directions to provide an air pathway to the chamber above a predetermined level of fluid collection in any orientation of the chamber.

2. A disposable liquid collection bag for collecting liquid from a suction tube and adapted for fluid tight insertion into a rigid suction chamber; which chamber is connected to a source of vacuum; said bag comprising:
 (a) a flexible plastic container having a liquid collecting port for providing an input port in fluid communication with said suction tube; and
 (b) a substantial portion of said container in proportion to the interior volume of said chamber being comprised of air permeable, liquid impermeable material, such that in any orientation of said chamber a surface area of said material will be exposed to vacuum in the chamber and will be above the level of the liquid collected in said bag.

3. The bag of claim 1 wherein the material extends in two dimensions longitudinally and transverse the central axis of the bag.

4. The bag of claim 2 wherein the bag is of planar construction formed of two plastic sheets sealed at their periphery with said material extending in two directions across a substantial portion of the length and width of at least one of said sheets.

5. The bag of claim 2 wherein the material extends in two dimensions longitudinally and transverse the central axis of the bag.

6. The bag of claim 2 wherein the liquid collecting port is coupled through a sealing cap; which cap seals the chamber.

* * * * *